United States Patent [19]

Mackal

[11] 4,205,417
[45] Jun. 3, 1980

[54] FERRULE

[76] Inventor: Glenn H. Mackal, Buena Vista Dr., Ringwood, N.J. 07456

[21] Appl. No.: 837,466

[22] Filed: Sep. 28, 1977

[51] Int. Cl.² .............................................. A44B 21/00
[52] U.S. Cl. .................................. 24/260; 24/115 M; 285/3; 285/323; 403/369
[58] Field of Search ................... 285/3, 4, 243, 256, 285/423, 255, 322, 323; 24/115 M, 114.5, 136 R, 260; 403/371, 369

[56] References Cited

U.S. PATENT DOCUMENTS

| 367,578 | 8/1887 | Babb | 285/322 |
|---|---|---|---|
| 613,903 | 11/1898 | Hussey | 285/322 |
| 688,698 | 12/1901 | Rupp | 285/322 |
| 2,147,239 | 2/1939 | Buchanan | 403/371 |
| 2,454,829 | 11/1948 | Neijstrom | 403/290 |
| 2,890,900 | 6/1959 | Williamson | 285/322 |
| 3,484,121 | 12/1969 | Quinton | 285/322 |
| 3,665,560 | 5/1972 | Bennett | 24/136 R |
| 3,724,882 | 4/1973 | Dehar | 285/322 |
| 3,932,918 | 1/1976 | Paskert | 24/260 |
| 4,022,497 | 5/1977 | Kotsakis | 285/4 |
| 4,090,463 | 5/1978 | Soderberg | 24/136 R |

FOREIGN PATENT DOCUMENTS

| 2108905 | 11/1971 | Fed. Rep. of Germany | 24/115 M |
|---|---|---|---|
| 163340 | 6/1921 | United Kingdom | 24/136 R |

*Primary Examiner*—William E. Lyddane

[57] ABSTRACT

There is disclosed a ferrule which is made of plastic material and is initially molded in one piece as a ferrule blank consisting of a thin-walled circular cylindrical shell or sleeve, a radially inwardly-directed transverse annular flange at the inner end of the sleeve, and a part which initially extends further axially inwardly from the flange, the said part having a plurality of axially extending fingers formed by straight-walled axial slots. The axially outer ends of the fingers are joined at their roots to the outer edge of the above-mentioned annular flange. The radially outer edge of such flange is joined to the axially inner end of the sleeve by a very narrow frangible annular flange. The fingers as initially molded diverge in an axially inwardly direction from their roots. Each of the fingers adjacent its inner end is provided with a peripheral groove which terminates at its inner end in a radially outwardly projecting lip. The inner surface of the sleeve is provided with an annular ridge at its axially inner end immediately adjacent the transverse flange on the ferrule.

8 Claims, 9 Drawing Figures

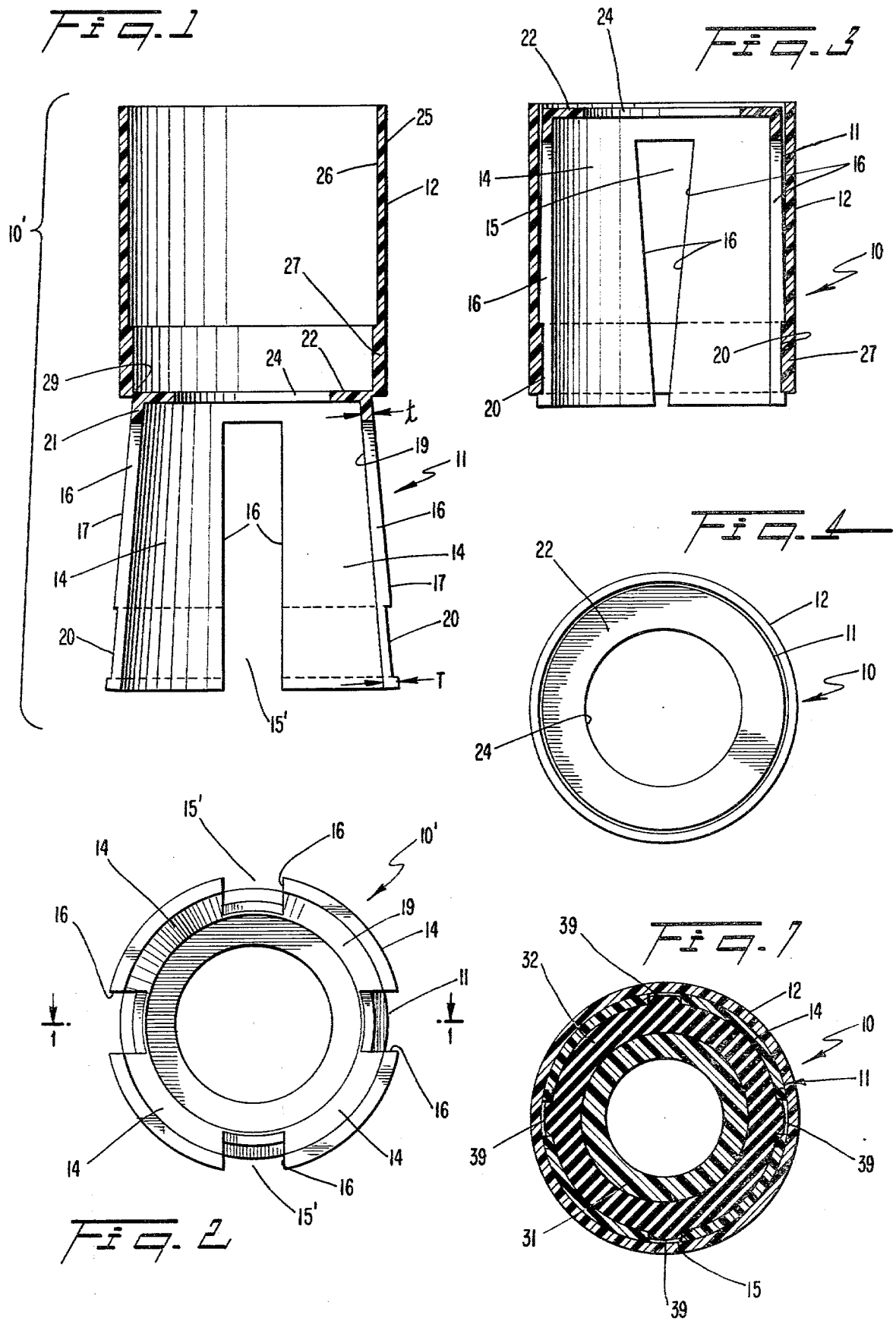

FERRULE

BACKGROUND OF THE INVENTION

In the illustrative embodiment disclosed herein, there is shown the outer end of a so-called balloon catheter which is retained within the bladder of a patient by inflating an outer balloon-like part of the catheter within the bladder. The balloon is usually inflated with sterile water. In order to maintain the water within the balloon, the outer end of the branch pipe leading to the balloon of the catheter is provided with a check valve which is telescoped into a branch tube of the catheter.

Difficulties have been experienced with former methods of retaining the valve in the branch tube. The V-branch tubing varies appreciably from piece to piece both in its inner and outer diameters. Because the rubber of the branch tube tends to stretch over appreciable periods, the valve frequently slips out of the tube unless it is retained therein by an adhesive or a crimped metal band or ferrule, and even then some difficulties have been experienced in securing satisfactory retention of the valve in the tube without injury to the tube or valve.

SUMMARY OF THE INVENTION

This invention relates to a ferrule blank, to the ferrule formed therefrom, to the assembly of the ferrule and the article or articles to which it is applied, and to the method of applying the ferrule blank and of assembling the parts of the ferrule.

The ferrule of the invention is made as a "blank" consisting of connected but unassembled portions or parts. The blank which is molded in one piece of plastic material has a first portion in the form of a thin-walled circular cylindrical shell or sleeve; a radially inwardly-directed transverse annular flange is disposed at the inner end of the sleeve. A second portion of the blank is in the form of an initially further axially inwardly located part having a plurality of axially extending fingers formed by straight-walled axial slots. The axially outer ends of the fingers are joined at their roots to the outer edge of the above-mentioned annular flange. The radially outer edge of such annular flange is joined to the axially inner end of the sleeve by a second, very narrow and thin frangible annular flange. The fingers as initially molded diverge in an axially inward direction from their roots. Each of the fingers increases in wall thickness in an axially inward direction, and adjacent its inner end is provided with a peripheral groove which terminates at its inner end in a radially outwardly projecting lip. The sleeve is provided with an annular ridge at its axially inner end immediately adjacent the transverse flange on the retainer.

The ferrule is used in the above-described application thereof as follows:

A valve, such as that shown in Mackal et al U.S. Pat. No. 3,831,629, is first inserted into the outer end of the branch tubing of the catheter. A ferrule blank is then telescoped over the valve, finger-end first, to a position in which the transverse flange of the blank engages the axially outer shoulder of the valve. A tool having two opposed jaws is then applied with a first jaw engaging the axially inner ends of the fingers and a second jaw engaging the axially outer end of the sleeve of the blank.

As the two jaws are moved relatively toward each other, the frangible flange of the ferrule is broken from the periphery of the transverse flange and the fingers connected thereto. The sleeves then slides axially inwardly over the transverse flange and the fingers until the sleeve lies coextensive with the transverse flange and fingers. In such position the annular ridge on the inner surface of the sleeve fits into the groove parts on the inner ends of the fingers, thereby to hold the parts of the retainer stably in place relative to each other.

Because the fingers are molded initially in an axially inwardly diverging relationship, when compressed by the sleeve in fully-mounted position in which their outer surfaces lie substantially along a circular cylinder, the axially inner ends of successive fingers substantially engage each other, and the former straight-walled groove between successive fingers now becomes a V-shaped opening between them, the closed end of the V being at the axially inner ends of the fingers. Such V-shaped openings permit excess rubber of the branch tube of the catheter to well thereinto, thus to form radial projections thereon which mechanically interlock with the V-shaped spaces between successive fingers of the mounted retainer.

BRIEF DESCRIPTION OF THE DRAWINGS

In the accompanying drawings:

FIG. 1 is a view in axial section through a one-piece blank for forming a ferrule, the section being taken along the line 1—1 in FIG. 2;

FIG. 2 is a view of the ferrule blank of FIG. 1 in bottom plan;

FIG. 3 is a view in vertical axial section through a ferrule which has been made from the blank of FIGS. 1 and 2;

FIG. 4 is a view in top plan of the ferrule of FIG. 3;

FIG. 7 is a view in section of the assembled ferrule and tube, the valve being shown in bottom plan, the section being taken along the line 7—7 in FIG. 6;

DETAILED DESCRIPTION

Figure 5:
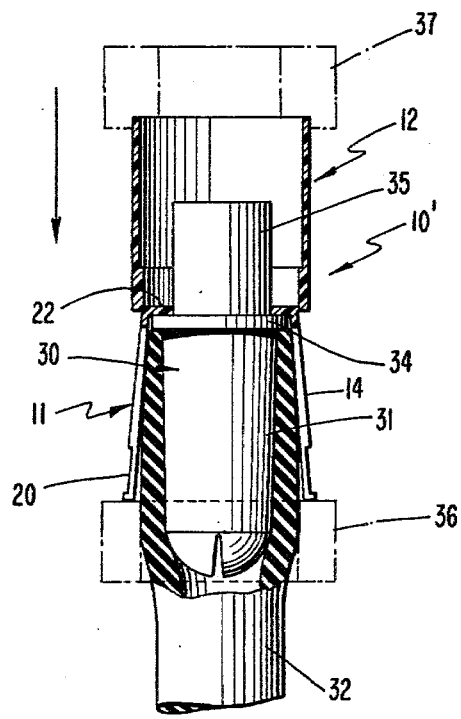
FIG. 5 is a view in vertical axial section of a ferrule blank initially positioned for mounting on the end of a tube containing a valve, the valve being shown in elevation, the opposed jaws of apparatus for assembling the parts of the ferrule being shown in phantom lines.

Turning now to the drawings, there is shown in FIG. 1 a ferrule blank generally designated 10', such blank having a lower (axially inner) part 11 and an upper (axially outer) part 12, the blank having been formed as an integral molding of plastic material. In a preferred embodiment, such plastic material is a linear polyoxymethylene-type acetyl resin sold under the trade name DELRIN. It is to be understood that the blank 10' may be made of other suitable materials. The portion 11 has a plurality (4 shown) of equally angularly spaced axially extending fingers 14, the fingers being separated by slots 15' having straight, axially extending parallel edges 16. The fingers have smooth outer surfaces 17 about the major portion of their length, and smooth inner surfaces 19 along their length, both the inner and outer surfaces 17 and 19, respectively, being arcuate in transverse section and substantially parallel. The wall thickness of the fingers 14 increases somewhat in an axially inward direction, thickness T somewhat exceeding thickness t, as shown. Near the axially inner end of each of the fingers there is formed a shallow transverse groove 20, the grooves 20 of the several fingers being transversely aligned. The fingers 14 extend axially inwardly from an annular root 21, root 21 being connected to a transverse radially inwardly extending annular flange 22 having a central hole 24 therethrough.

The axially outer portion 12 of the ferrule blank 10' is generally in the form of a thin-walled hollow cylinder or sleeve having a smooth outer wall 25 and a smooth inner wall 26 throughout the predominant portion of its axial length. At its axially inner end the portion 12 has a transverse annular ridge 27 the cross-section of which is substantially complementary to the cross-section of the groove parts 20 so as to interfit therewith when the parts of the ferrule are assembled. It is to be noted that both the groove 20 and the ridge 27 are bounded by sharp transverse annular or part-annular surfaces so as to effectively lock the parts 11 and 12 of the ferrule together against relative axial movement after they have been assembled. In the ferrule blank 10' the axially and radially outer edge of the annular root 21 of part 11 is integrally connected to the radially and axially inner edge of the sleeve 12 by a thin frangible annular flange 29.

Figure 8:
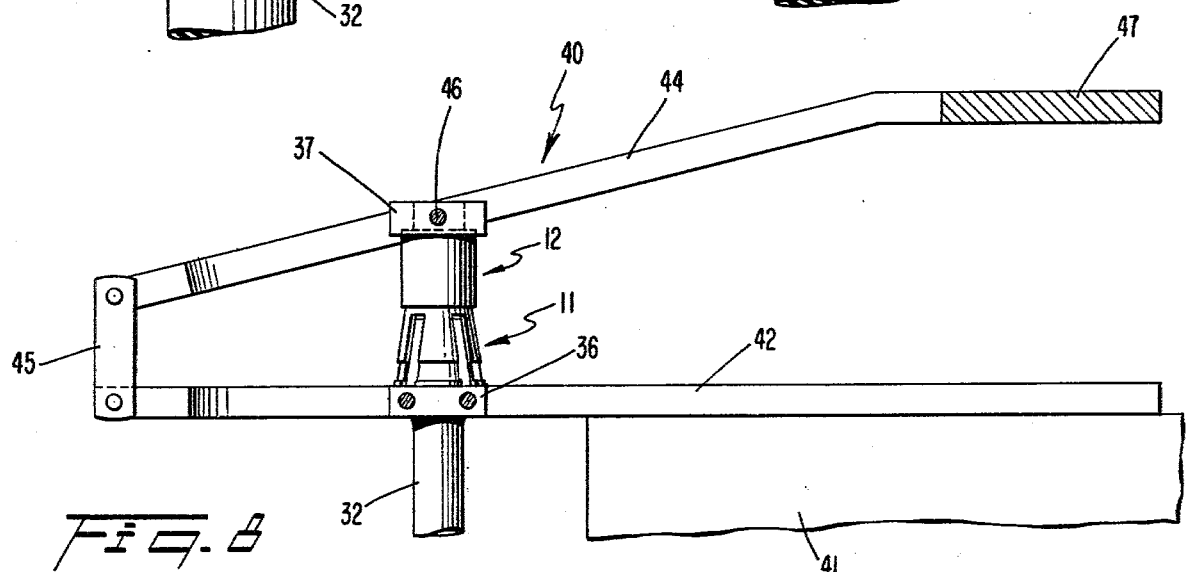
FIG. 8 is a view in side elevation of apparatus for applying a ferrule blank to an assembled tube and valve and for forming the ferrule from the blank.

When the ferrule blank is mounted upon an article, such as an assembly of a tube and valve, in the manner shown in FIGS. 5 and 8, and the opposite ends of the ferrule blank are subjected to forces which tend to move them toward each other, the flange 29 is broken, and the sleeve 12 is telescoped over the part 11 of the ferrule to bring the parts into the relative positions thereof shown in FIGS. 3, 4, and 7. The tube and valve are omitted from FIGS. 3 and 4 for clarity of illustration of the assembled ferrule. As shown in FIGS. 3 and 4, the telescoping of the sleeve 12 over the part 11 causes the initially axially inwardly diverging fingers 14 to be thrust progressively radially inwardly to a position in which they still diverge slightly but lie almost upon a circular cylinder when the ridge 27 is received within the grooves 20 at the axially inner ends of the fingers 14. The inherent resilience of the plastic material of which the blank 10' is made, plus the resilience of the rubber tube upon which the ferrule is mounted, strongly urge the axially inner ends of the fingers 14 radially outwardly so that the ridge 27 is stably held in the grooves 20.

As shown in FIG. 3, the initially parallel edged slots 15' have now become generally V-shaped slots 15, the edges of which converge in an axially inward direction. Slots 15 aid in the secure retention of ferrule upon the article, such as a rubber tube, upon which it is mounted, as will be explained more fully in connection with FIG. 7.

In FIG. 5 there is shown a check valve 30 having a body 31, the valve being telescoped within the outer end of a rubber or rubber-like tube 32. Valve 31 has a flange 34 thereon which abuts the outer end of the tube, the body having an axially outwardly extending hood 35 thereon. The ferrule blank 10' is applied to the assembly of tube and valve in the manner shown, with the fingers 14 telescoped over the end of the tube, and with the hood 35 of the valve extending axially upwardly outwardly through the central hole 24 in the annular flange 22 of the ferrule blank. The lowest ends of the fingers 14 are engaged by a lower jaw 36 and the upper end of the sleeve 12 is engaged by an upper jaw 37.

Figure 6:
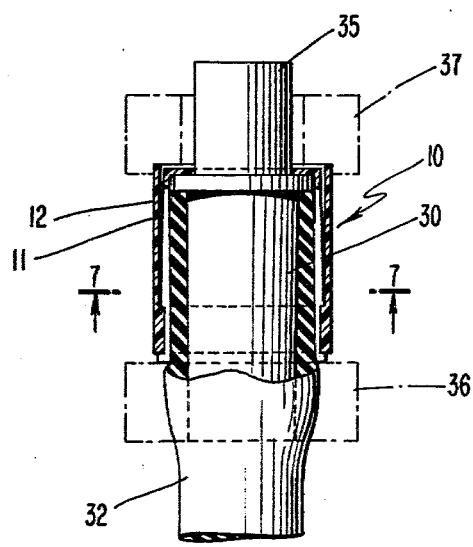
FIG. 6 is a view similar to FIG. 5 but with the frangible connection between the parts of the ferrule blank having been broken and the parts of the ferrule blank having been assembled to form a ferrule applied to the end of the tube.

The jaws 36 and 37 are now advanced axially toward each other so that the frangible flange 29 is broken and the sleeve 12 is telescoped over the portion 11 of the ferrule to bring the parts to the relative positions thereof shown in FIGS. 6 and 7.

FIG. 7 shows the manner in which the V-shaped slots 15 contribute substantially to the total gripping effect exerted by the ferrule upon the tube 32. As there shown, the telescoping of the sleeve 12 over the fingers 14 of portion 11 of the ferrule markedly radially compresses the tube 32 thereby causing the excess portions of such tube to well radially outwardly into projections 39 which extend into the grooves 15. Because of the V-shape of the grooves 15, projections 39 in effect key into such grooves and retain the assembled ferrule 10' from being axially withdrawn therefrom.

Figure 9:
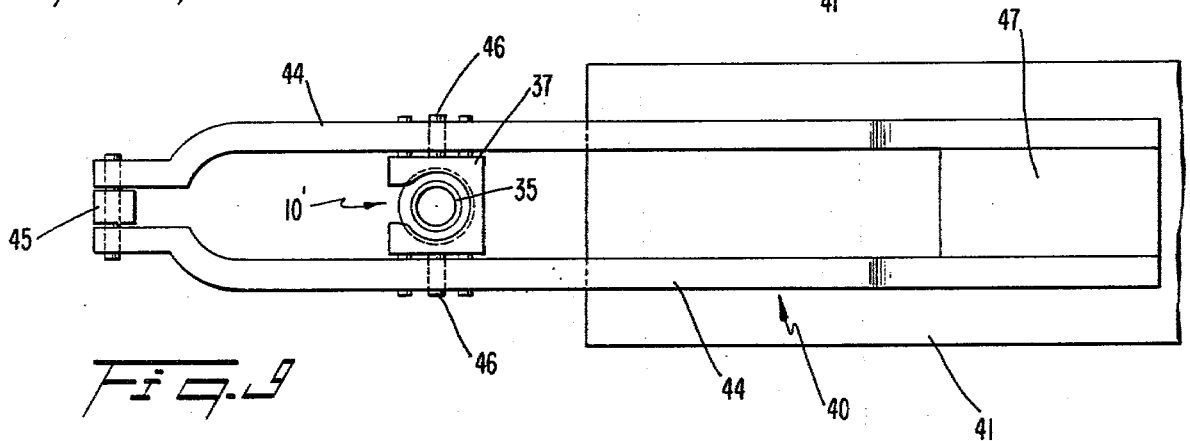
FIG. 9 is a view in plan of the apparatus shown in FIG. 8, but omitting the valve, tube, and ferrule blank.

The jaws 36 and 37 may be mounted and actuated in a number of ways; the apparatus 40 shown in FIGS. 8 and 9 is merely illustrative. Such apparatus, which is shown on a support 41, is made up of two parallel lower rods 42 the left-hand ends of which are bent in to approach each other. Two generally similar upper rods 44 are likewise bent in to approach each other at their left-hand ends, the upper and lower rods being pivotally connected at such left-hand ends by a short upstanding rod or plate 45. The lower jaw 36 is disposed between the two lower rods 42 and is affixed thereto. The upper jaw 37 is disposed between the two upper rods 44 and is pivotally connected thereto by pivot pins 46. The right-hand ends of the upper rods 44 are bent to lie generally horizontal, and are connected by a filler piece to form a handle 47. It will be obvious that with the parts mounted as shown in FIG. 8, the operator presses the handle 47 downwardly so that the upper jaw 37 is thrust downwardly toward the lower jaw 36 to effect the assembly of the parts of the ferrule as shown in FIGS. 6 and 7.

It is to be understood that the ferrule of the invention can be employed in a number of applications which are different from that described above. Thus, for example, the ferrule may form a cap sealing the end of a tube by making the flange 22 in the form of an imperforate disc which extends completely across and seals the end of the tube. The ferrule can also be applied to rod-like articles, other than an assembly of a tube and valve or the like, to protect an end of such article.

Although the invention is illustrated and described with reference to a preferred plurality of embodiments, it is to be expressly understood that it is in no way limited by the disclosure of such a plurality of embodiments, but is capable of numerous modifications within the scope of the appended claims.

What is claimed is:

1. A device which, when applied to a rod-like article, becomes a composite ferrule, said device comprising a first member, the first member having a body with a peripherally extending portion, a plurality of axially inwardly extending angularly spaced fingers joined at their axially outer ends to the peripherally extending portion of the body, the first member being adapted to be mounted upon the rod-like article with the fingers lying radially outwardly alongside the outer surface of the article and generally parallel to the longitudinal axis thereof, and a second member in the form of a sleeve adapted to be telescoped over the body and fingers of the thus-mounted first member to thrust the fingers radially inwardly into gripping relationship with the article, before the device is applied to an article the first and second members being connected by frangible means, the members being disposed in coaxial relationship with the second member disposed axially downwardly of the first member.

2. A device according to claim 1, wherein the axially inner end of the second member is frangibly connected to the periphery of the body of the first member.

3. A device according to claim 2, wherein the frangible connection between the first and second members is ruptured by relative axial movement of the two members toward each other.

4. A device according to claim 1, wherein the first and second members and the frangible connecting means therebetween are formed integrally.

5. A device according to claim 1, wherein the first and second members and the frangible connecting means therebetween are molded integrally of plastic material.

6. A device according to claim 1, comprising means for locking the first and second members against relative axial movement when such members are fully telescoped, said locking means comprising a projection on one of the first and second members and a recess on the other of the first and second members, the projection and recess interfitting when the first and second members are fully applied to form a composite ferrule.

7. A device according to claim 6, wherein the projection is in the form of a peripherally extending radially inwardly projecting ridge on the radially inner wall of the second member, and the recess is a peripherally extending groove on the radially outer surface of at least one of the fingers of the first member.

8. A device according to claim 7, wherein each finger is peripherally grooved adjacent its axially inner end, the grooves on the fingers receiving the ridge on the second member.

* * * * *